(12) United States Patent
Berger et al.

(10) Patent No.: US 12,077,168 B2
(45) Date of Patent: Sep. 3, 2024

(54) OPERATIONAL ASSISTANCE METHOD FOR A VEHICLE, CONTROL UNIT, AND VEHICLE

(71) Applicant: Bayerische Motoren Werke Aktiengesellschaft, Munich (DE)

(72) Inventors: Tobias Berger, Moers (DE); Georg Burkhard, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 318 days.

(21) Appl. No.: 17/597,212

(22) PCT Filed: Aug. 11, 2020

(86) PCT No.: PCT/EP2020/072501
§ 371 (c)(1),
(2) Date: Dec. 29, 2021

(87) PCT Pub. No.: WO2021/037555
PCT Pub. Date: Mar. 4, 2021

(65) Prior Publication Data
US 2022/0242417 A1   Aug. 4, 2022

(30) Foreign Application Priority Data
Aug. 27, 2019  (DE) ..................... 10 2019 122 907.3

(51) Int. Cl.
*B60W 40/09* (2012.01)
*B60W 40/107* (2012.01)
*G06V 20/59* (2022.01)

(52) U.S. Cl.
CPC .......... *B60W 40/09* (2013.01); *B60W 40/107* (2013.01); *G06V 20/597* (2022.01);
(Continued)

(58) Field of Classification Search
CPC .............. B60W 40/09; B60W 40/107; B60W 2420/403; B60W 2420/905;
(Continued)

(56) References Cited

U.S. PATENT DOCUMENTS

| 5,536,059 A | * | 7/1996 | Amirouche | ............ | B60N 2/501 296/65.02 |
| 2002/0116104 A1 | * | 8/2002 | Kawashima | ........... | B60G 7/006 280/5.515 |

(Continued)

FOREIGN PATENT DOCUMENTS

| DE | 10 2007 019 366 A1 | 10/2008 |
| DE | 10 2017 206 012 B3 | 7/2018 |

(Continued)

OTHER PUBLICATIONS

International Search Report (PCT/ISA/210) issued in PCT Application No. PCT/EP2020/072501 dated Dec. 7, 2020 with English translation (seven (7) pages).

(Continued)

*Primary Examiner* — Tyler D Paige
(74) *Attorney, Agent, or Firm* — Crowell & Moring LLP

(57) ABSTRACT

An operational assistance method for a vehicle, in particular for a motor vehicle, is provided. A movement of an area of a body of a vehicle occupant is captured and sensor values representative of the movement are provided, sensor values for an area of the body of a vehicle occupant are weighted with one another and are combined to form an acceleration value, and the acceleration value is provided. A weighting factor for a respective sensor value, as the degree of the weighting of the sensor value in the acceleration value, is dependent on the magnitude of the sensor value.

18 Claims, 5 Drawing Sheets

(52) U.S. Cl.
CPC . *B60W 2420/403* (2013.01); *B60W 2420/905* (2013.01); *B60W 2520/105* (2013.01)

(58) Field of Classification Search
CPC ........... B60W 2520/105; B60W 10/22; B60W 30/025; B60W 40/10; B60W 50/0098; B60W 40/08; B60W 2540/00; G06V 20/597; B60G 2206/99; B60G 2400/10; B60G 2400/62; B60G 2400/90; B60G 2400/96; B60G 2500/10; B60G 2600/172; B60G 2800/162; B60T 2260/06; A61B 5/1114; A61B 5/18; A61B 5/6893; A61B 5/7264; B60R 16/037; B60R 16/0231; B60N 2/90
USPC ............................................................ 701/1
See application file for complete search history.

(56) References Cited

U.S. PATENT DOCUMENTS

| | | | | |
|---|---|---|---|---|
| 2008/0258522 | A1* | 10/2008 | Meyder | G01H 3/14 297/217.3 |
| 2014/0297116 | A1* | 10/2014 | Anderson | H02K 29/08 701/37 |
| 2017/0136842 | A1* | 5/2017 | Anderson | B60G 17/0162 |
| 2018/0022361 | A1* | 1/2018 | Rao | B60R 16/037 701/23 |
| 2021/0114553 | A1* | 4/2021 | Awtar | B60R 16/037 |

FOREIGN PATENT DOCUMENTS

| | | |
|---|---|---|
| DE | 10 2018 203 433 A1 | 9/2019 |
| WO | WO 2016/197068 A1 | 12/2016 |
| WO | WO 2018/169861 A1 | 9/2018 |

OTHER PUBLICATIONS

German-language Written Opinion (PCT/ISA/237) issued in PCT Application No. PCT/EP2020/072501 dated Dec. 7, 2020 (five (5) pages).

German-language Search Report issued in German Application No. 10 2019 122 907.3 dated Mar. 16, 2020 with partial English translation (10 pages).

* cited by examiner

OPERATIONAL ASSISTANCE METHOD FOR A VEHICLE, CONTROL UNIT, AND VEHICLE

BACKGROUND AND SUMMARY OF THE INVENTION

The present invention relates to an operational assistance method for a vehicle, in particular for a motor vehicle, to a control unit, in particular for a vehicle or motor vehicle, and to a vehicle or a motor vehicle per se.

It is known, for example in accordance with the ISO-2631 standard, for forces and accelerations acting on an occupant in the vehicle to be detected by way of measurement points on or in the vehicle in order to determine driving comfort. However, in the case of the conventional approach, objective criteria can be represented only with insufficient reliability, and corresponding data are insufficient for partially or fully autonomous driving and for corresponding operational assistance methods.

The invention is based on the object of specifying an operational assistance method, a control unit and a vehicle, in the case of which values of accelerations acting on an occupant of a vehicle can be determined and made available in a reliable and objective manner and with relatively simple techniques. The method proposed with embodiments of the invention can primarily be used in particular for objectifying the influence of vibrations and thus the vibrational comfort, in particular with regard to vertical excitations and movements. Here, an assessment and/or transferability to movements and vibrations in the transverse and/or longitudinal direction, or one or more arbitrary combinations of the three movement directions, is alternatively or additionally possible.

The object on which the invention is based is achieved according to the claimed invention.

According to a first aspect of the present invention, an operational assistance method for a vehicle and in particular for a motor vehicle is created, in which
  (i) a movement of a region of a body of a vehicle occupant is detected and sensor values representative of the movement are made available,
  (ii) sensor values relating to a region of the body of a vehicle occupant are weighted with one another and combined to form an acceleration value, and
  (iii) the acceleration value is made available.

According to an embodiment of the invention, a weighting factor for a respective sensor value as a degree of the weighting of the sensor value in the acceleration value is dependent on the magnitude of the sensor value.

A particularly high degree of objectification is achieved in a preferred embodiment of the method according to the invention if a movement of one or more occupants is compared with a movement of the vehicle. In this way, it is for example possible to assess the movement for plausibility, for example also in the context of discriminating occupant movements induced by the vehicle movement from voluntary movements of an occupant, for example in the case of some form of activity in the interior compartment of the vehicle. The processes, described below, of the weighting and in particular the determination and the selection of the weighting factors may also be made dependent on this.

In one advantageous refinement of the operational assistance method according to the invention, in a manner dependent on the magnitude of a sensor value, a weighting factor for the sensor value may be selected from a set of a—in particular discrete—plurality of weighting factors. This may for example be performed on the basis of a single-stage or multi-stage comparison of the magnitude of the sensor value with one or more limit values or threshold values.

In addition or alternatively, the determination and/or selection of the weighting factors may be performed in a manner dependent on the magnitude of the sensor values such that higher sensor values tend to be given greater consideration than lower sensor values, in particular in a variable manner and/or in a manner dependent on additional parameters, such as the driving dynamics of the vehicle, on biometric and/or personal data of the occupant.

In another advantageous exemplary embodiment of the method according to the invention, sensor values relating to a region of the body are detected—in particular with bandpass filtering—as RMS values, in particular separately for each spatial degree of freedom. This may mean in particular that, for translational movements, the three spatial translation directions x, y, z of an underlying coordinate system are taken into consideration separately and optionally combined with one another. Correspondingly, for rotational movements, components of the rotation about the respective axes x, y, z of the underlying coordinate system as axes of rotation may be taken into consideration separately and optionally combined with one another. This offers the advantage that movements can be considered in relation to one another. For example, a rolling movement is perceived as a highly unpleasant movement. In combination with a lifting movement, however, this may have only a small influence, or no influence whatsoever, on the state of an occupant. Thus, if a rolling movement component is small, or if a pitching movement occurs instead, a lifting movement can increase in importance in the perception of comfort and the assessment thereof. This can be correspondingly taken into consideration—optionally in individually adapted fashion—in embodiments of the invention.

Here, it is additionally or alternatively conceivable that, in another advantageous refinement of the method according to the invention, sensor values relating to a region of the body for translational and for rotational degrees of freedom are in each case separately combined with one another, in particular in each case as an RMS value. It is thus possible, for example, for translational movements and rotational movements to be taken into consideration independently of one another, and optionally differently weighted.

Even though basically all regions or parts of the human body are involved in an occupant movement, the head of the person, as the location of the organ of equilibrium and the eyes, is of particular importance. Therefore, in a particularly advantageous refinement of the method according to the invention, it is provided that, as a region of the body, the head is detected with regard to the movement and/or acceleration components with the sensor values.

It is however additionally or alternatively also possible for one or more limbs, the chest and/or the thighs of an occupant to be detected and taken into consideration by virtue of the movement thereof being detected with regard to translation and/or rotation by way of an underlying sensor unit. This approach is advantageous inter alia because vibrations and movements additionally have an influence on the perception of comfort by way of pressure areas and the natural frequencies of organs, and according to an embodiment of the invention, this influence can be taken into consideration in the assessment and objectification in embodiments of the method.

To allow better objectivity of the values detected by measurement, it is expedient that, according to another exemplary embodiment of the method according to the invention, an acceleration value is assigned a comfort value from a—in particular discrete—comfort scale with a plurality of disjoint intervals of acceleration values with interval limits. This means in particular that the determined acceleration values are compared with intervals and, on the basis of the comparison and thus in particular the presence in an interval, a corresponding comfort value is determined and optionally made available, for example in order to deliver an actual assessment of the comfort of an occupant during operation of a vehicle and optionally use this as a basis for closed-loop or open-loop control of the vehicle and/or in a process of designing vehicle components, for example in a planning process, a modelling process or the production process.

According to another refinement of the present invention, the interval limits can be determined by way of a clustering method and in particular by way of a K-means method or alternatively by way of an optimization method, a brute force and/or a trial and error method, optionally empirically or partly empirically. By way of these measures, it is possible to achieve a more realistic image of corresponding movement influences on an occupant, with an improved degree of objectification.

In order to assist and/or carry out such a method, in preferred embodiments of the invention, it is for example possible for targeted field studies and/or driving simulator studies to be carried out for the purposes of obtaining data. Alternatively or in addition, customer surveys may be carried out, for example during a journey and/or by way of a form of feedback service. It is advantageous if, here, a movement of the vehicle and/or of the occupant and the comfort value, and/or the evaluation and/or raw data associated therewith, are detected simultaneously (or approximately simultaneously) and/or over the same period of time.

In addition or alternatively, and likewise in order to improve a realistic and objectified assessment, it is possible according to another advantageous embodiment of the method according to the invention for limit values or threshold values for a single-stage or multi-stage comparison for the determination and/or selection of weighting factors, and/or weighting factors themselves, to be determined by way of a clustering method and in particular by way of a K-means method.

Preferably, the weighting factors themselves may also be determined by way of a clustering method and in particular by way of a K-means method.

The determined acceleration values, which are optionally made available, are suitable for a large number of possible uses.

On the one hand, it is conceivable for a respective acceleration value and/or a comfort value or a signal derived therefrom to be supplied to a vehicle control system and in particular to an actuator of an underlying vehicle for the operational control thereof. This may be utilized in particular for damping control of the vehicle.

It is additionally or alternatively conceivable for a respective acceleration value and/or a comfort value or a signal derived therefrom to be used for determining a chassis model and/or in a planning and/or production method, for example in order to achieve an improvement of vehicle components already in the planning and production phase.

According to another aspect of the present invention, a control unit is created which may be designed in particular for a vehicle or motor vehicle and which is configured to initiate, trigger, execute or control in open-loop and/or closed-loop fashion an operational assistance method according to an embodiment of the invention.

A control unit of said type may be implemented on the basis, or with the involvement, of hardware, for example with or composed of an ASIC and/or with or composed of a discrete circuit. Alternatively or in addition, a partial or complete implementation as a computer-assisted method, that is to say in the form of software, is also conceivable.

An embodiment of present invention furthermore includes a vehicle and in particular motor vehicle per se, which are configured to be controlled and/or used with an operational assistance method according to an embodiment of the invention and/or which have a control unit configured according to an embodiment of the invention.

Further details, features and advantages of the invention will emerge from the following description and from the figures.

DETAILED DESCRIPTION OF THE DRAWINGS

Figure 1:
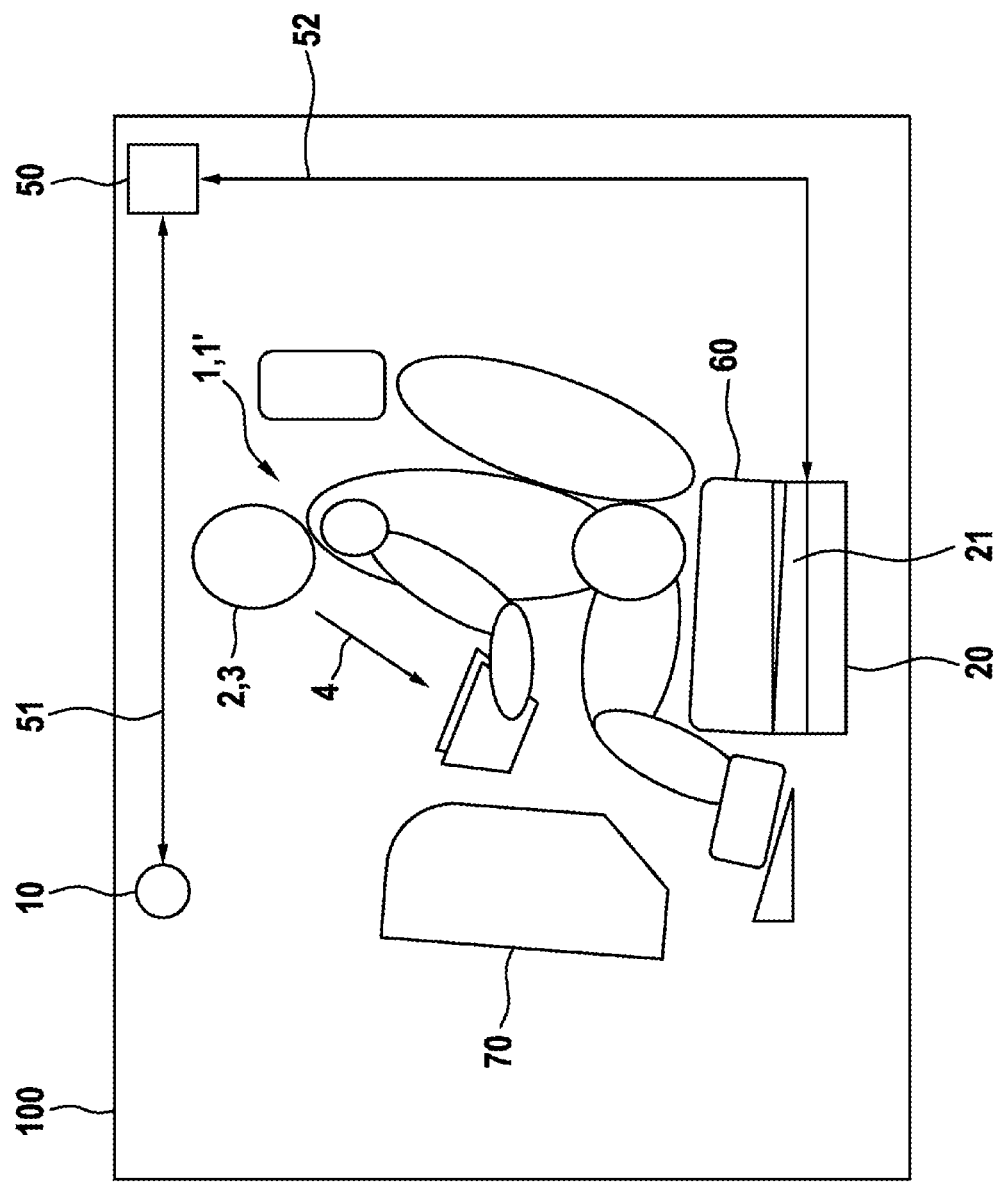
FIGS. 1 and 2 show, in the form of schematic and sectional side views, embodiments of a vehicle according to the invention.

Exemplary embodiments and the technical background of the invention will be described in detail below with reference to FIGS. 1 to 4b. Identical and equivalent elements and components, or elements and components of identical or equivalent action, will be denoted by the same reference designations. A detailed description of the designated elements and components will not be given every time they are mentioned.

The illustrated features and further characteristics may be isolated from one another in any form and combined with one another in any desired manner without departing from the core of the invention.

The invention may be classified in particular—but not exclusively—in the context of partially or fully autonomous driving.

Firstly, reference will be made very generally to FIGS. 1 to 3.

By contrast to the situation in manually operated vehicles 100, the vehicle occupants 1' no longer need to actively and/or attentively follow or control the driving operation during autonomous travel. The occupants 1' can therefore pursue other activities.

Against the background of a correspondingly changed driving experience—specifically the preoccupation with other things during travel, wherein attention is not directed to the road and the vehicle occupant 1' is not prepared in good time for the route ahead including possible acceleration events—this presents new challenges with regard to driving comfort and driving dynamics.

The evaluation and objectification of driving comfort in vehicles 100, and in particular in partially or fully autonomously driving vehicles 100, are thus also of increasing importance.

The hitherto best results regarding the objectification of driving comfort can be achieved by way of the methods described in ISO-2631. This relates to the evaluation of whole-body vibrations, for example in a frequency range from 0.5 Hz to 80 Hz, with regard to health and comfort. Here, according to ISO-2631, accelerations at the following measurement points on the human body 1 and on the vehicle 100 are taken into consideration: armrest, seat cushion, seat surface, backrest of a vehicle seat 60, and feet. The head 3 or body of the driver or occupant 1' in general is not taken into consideration as a measurement point.

Figure 3:
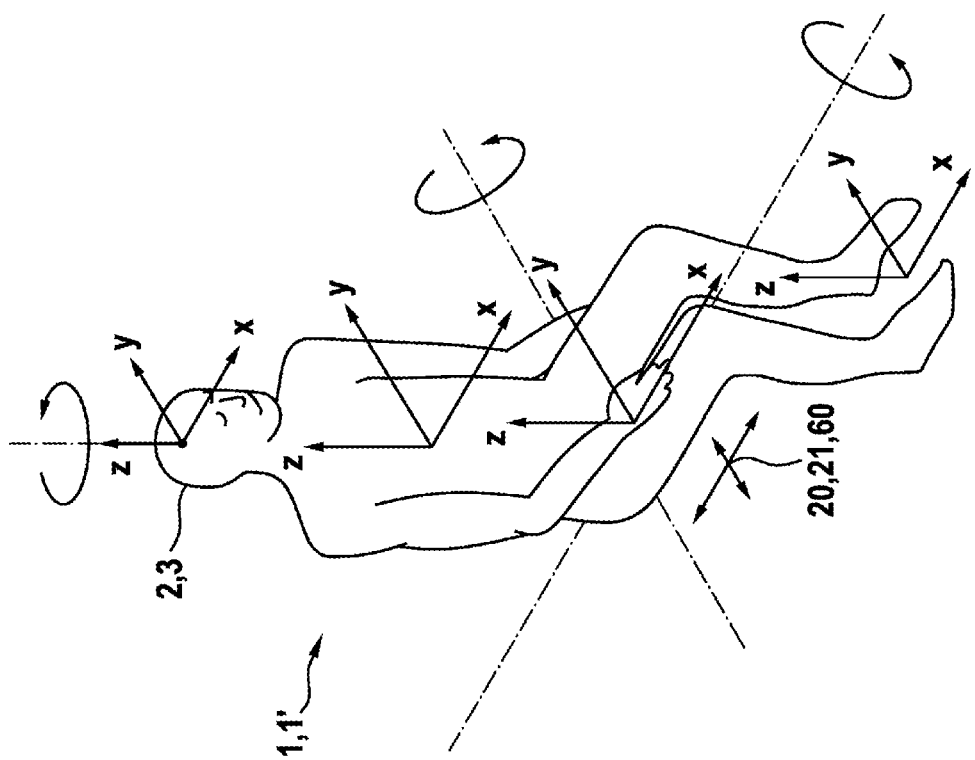
FIG. 3 shows, in a perspective view, a person as an occupant of a vehicle configured according to an embodiment of the invention, for the purposes of explaining different forms of movement that can be detected in accordance with the invention.

The detected accelerations may include not only the acceleration values in all three spatial directions x, y, z but also angular speeds or rates of rotation about the axes x, y, z, as per FIG. 3. In this regard, FIG. 3 shows, in the form of a perspective view, the body 1 of a person as an occupant 1' of a vehicle 100 configured according to an embodiment of the invention, for the purposes of explaining different forms of movement that can be detected in accordance with an embodiment of the invention.

It can be seen that a total of six degrees of freedom exist for each measurement point, that is to say for each region 2 of the body 1 of an occupant 1', wherein, in particular, a frequency-dependent function may be taken into consideration.

The most important parameter for evaluating comfort is conventionally the occurring vibration, with an overall vibration value.

The overall vibration value is conventionally determined by detecting the vibrations at the respective measurement points as input values (inputs), by weighting and/or selecting (rating) of the input values in a fixedly specified manner, for example in a manner dependent on the frequency of the vibration, by filtering data, for example for the purposes of filtering out invalid values, for example accelerations above a threshold value, by calculating the root mean square (RMS) of the vibrations over a specified time period for each measurement point, by weighting the RMS values of the individual measurement points with conventionally previously specified weighting factors k, and by adding the weighted RMS values to form an overall vibration value.

The overall vibration value is subsequently compared with an evaluation scale relating to comfort, in order, in a categorization process, to make a statement regarding the overall level of comfort experienced.

Disadvantages of the conventional approach are inter alia the following aspects:

The evaluation scale proposed according to ISO-2631 has no distinct boundaries between the respective ranges or gradations of comfort. The range boundaries overlap and do not allow a distinct statement to be made. The lack of distinction in turn allows a subjective interpretation.

Additionally, the approach according to ISO-2531 does not take into consideration important measurement points on the head 3 or on the rest of the body 1 of the occupant 1', which are however of high relevance in the context of autonomous driving.

The fixedly preset weightings of the movement directions do not allow any flexibility in the assessment and objectification, wherein personal needs of a respective occupant 1' cannot be taken into consideration either.

The overlapping intervals or boundaries of the conventional comfort scale prevent an objectification and open the door to a subjective interpretation, specifically owing to the lack of distinction of the assessment.

One aspect of the present invention relates inter alia to an enhancement of the approach according to the ISO-2631 standard.

It is an aim of the enhanced method according to an embodiment of the invention to create a more objective and/or improved assessment of comfort for vehicle occupants 1'—in particular in the case of autonomous driving— which in particular also comes as close as possible to a subjectively experienced perception of comfort.

The incorporation of additional measurement points, in particular on the head 3 as a region 2 of the body 1 of an occupant 1', the specification of a comfort scale with clearly defined and/or non-overlapping boundaries or intervals and/or the use of mathematical methods for further objectifying the assessment of comfort can be regarded as essential aspects of an embodiment of the invention.

Components used, and in particular hardware aspects, will be described in detail in conjunction with FIGS. 1 and 2.

Figure 2:
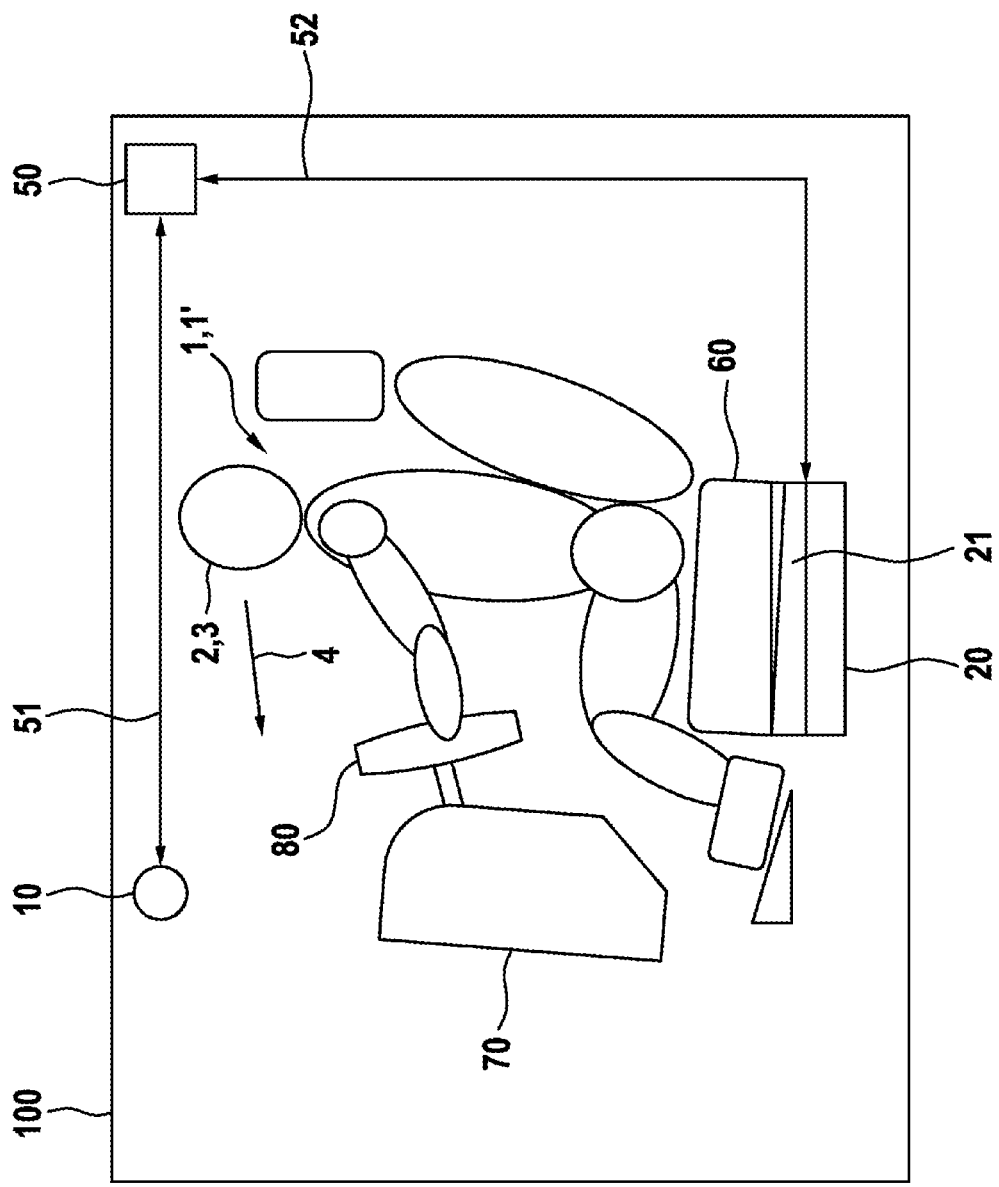

In this regard, FIGS. 1 and 2 show, in the form of schematic and sectional side views, embodiments of a vehicle 100 according to the invention such as may be used in the operational assistance method according to embodiments of the invention.

A body measurement system is used to detect the occurring accelerations. Said body measurement system serves for recording the occupant movements during real and/or simulated travel.

The system may have one or more movement sensors 10 or sensor units 10, for example on the head 3, chest or other regions 2 of the body 1 of an occupant 1' and/or on components of the vehicle 100, for example in conjunction with a vehicle seat 60, a seat cushion, a backrest and a seat rail. The latter may also serve for the discrimination of voluntary movements of the occupant 1'.

The detection is possible not only by way of local contact-type sensors and/or sensors worn on the body but also in contactless fashion, for example by way of optical sensors, cameras or the like.

A respective sensor unit 10 is operatively connected via a first control and/or detection line 51 to a control unit 50, in which an embodiment of the operational assistance method according to the invention can be executed or by way of which said embodiment can be initiated or controlled in open-loop or closed-loop fashion.

Furthermore, the control unit 50 is operatively connected via a second control and/or detection line 52 to a vehicle control system 20, and in particular to an actuator 21, in this case for example for influencing the vehicle seat 60.

In the embodiment as per FIG. 1, the viewing direction 4 of the occupant 1' is directed not to the traffic or to the surroundings of the vehicle but rather either to the console 70, which may comprise a multimedia unit for viewing media, or the occupant 1' is engrossed in reading material and is not actively involved in the traffic situation.

The embodiment as per FIG. 2 may involve a partially autonomously driving vehicle 100, in which the occupant 1' is not fully but only sporadically involved in the control of the vehicle, for example for steering corrections using the steering wheel 80. The method according to an embodiment of the invention can however also be advantageously used here, and also in the case of non-autonomously driving vehicles, for the purposes of improving driving comfort for occupants 1' who are not in control of the vehicle, or for sensitive drivers.

According to an embodiment of the invention, the measurement concept may be enhanced to include any measurement points.

In order to make recorded movement data of vehicle 100 and vehicle occupants 1' (or head 3) comparable, the coordinates may be transformed into a unitary coordinate system—for example global or fixed with respect to the vehicle. The data are subsequently synchronized and divided up in accordance with the individual driving situations.

Figure 4A:
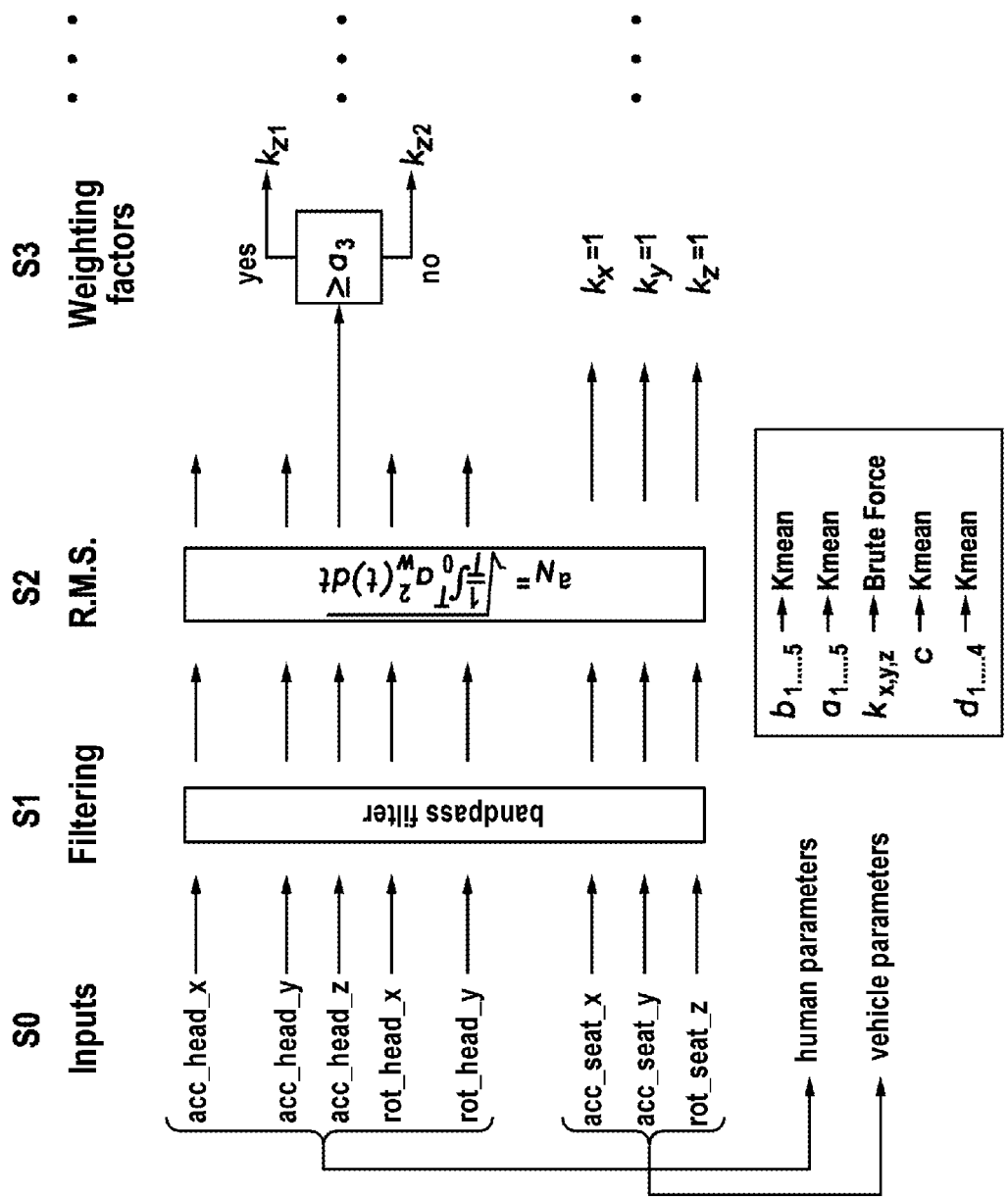
FIGS. 4a and 4b show, in a table, aspects of an embodiment of the operational assistance method according to the invention.
Figure 4B:
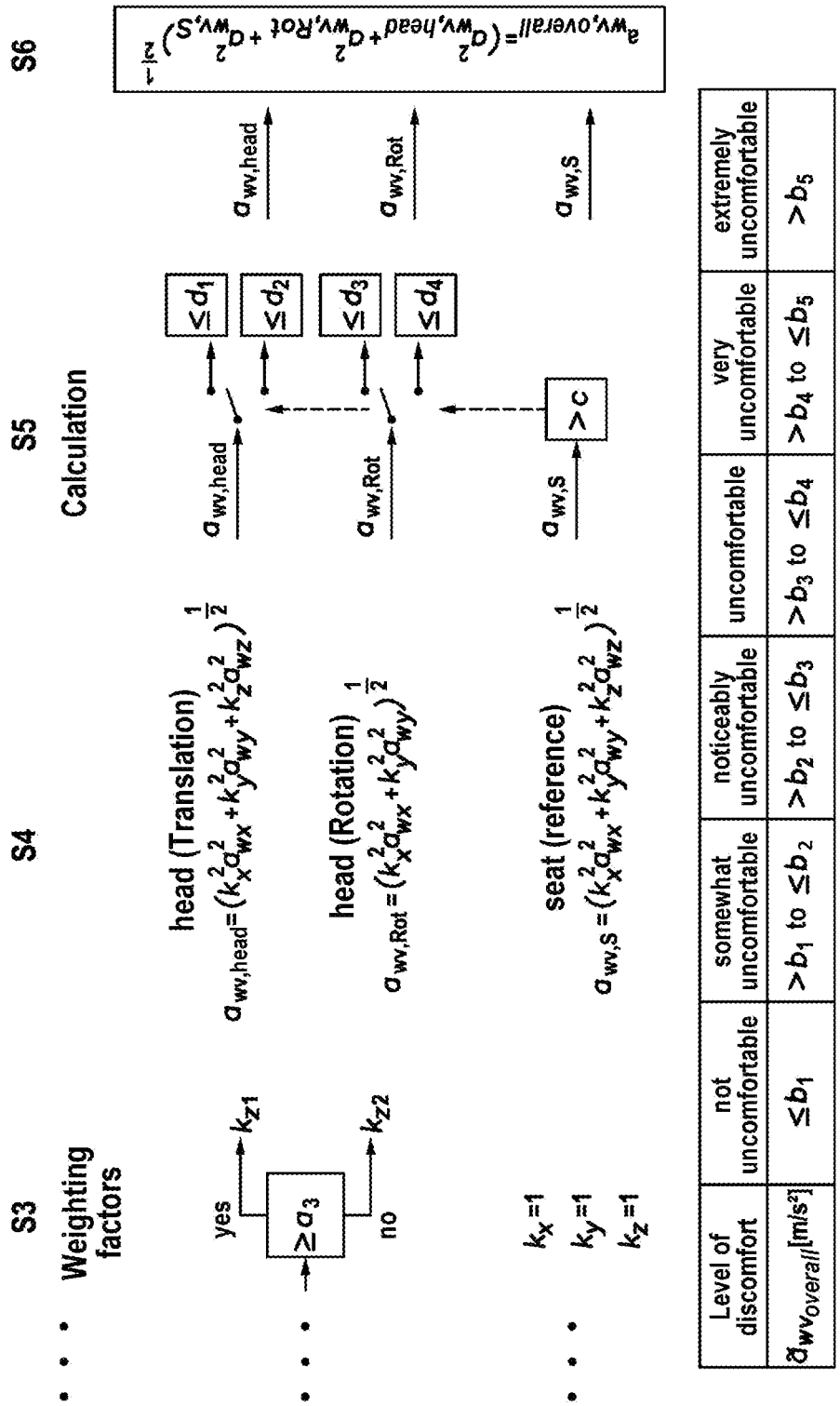

One embodiment of the operational assistance method according to the invention can be gathered inter alia from FIGS. 4a and 4b, which show aspects of the operational assistance method according to an embodiment of the invention in the form of a table.

Here, after the detection S0 of the measurement values as input values or inputs, for example with in each case one acceleration value acc_Head_x, acc_Heady, acc_Head_z from translational movements for the head in the directions x, y, z, in each case one acceleration value rot_Head_x, rot_Head_y from rotational movements for the head about the axes x, y and in each case one acceleration value acc_Seat_x, acc_Seat_y, acc_Seat_z from translational movements for the seat in the directions x, y, z, the latter specifically as a reference, the following steps can be carried out:

- Bandpass filtering S1 of the detected data, in particular in order to eliminate invalid measurement values and/or taking into consideration a frequency band in the range from approximately 0.5 Hz to approximately 80 Hz.
- Calculating S2 RMS values for the respective input values or inputs, in particular in the form of an average with respect to time over a specified time period T. Resulting RMS values are in each case average acceleration values $a_{wx}$, $a_{wy}$, $a_{wz}$, specifically relating to each spatial direction X, Y, Z with respect to translation and rotation and with respect to the respective body part, in this case for example the head, and the reference position, in this case for example the seat.
- The respective RMS values are weighted S4 in an overall value, with corresponding determination and/or selection S3 of the weighting factors; for example, the higher the RMS value, the higher its weighting in the overall value, in particular by way of weighting factors that are also referred to as k factors. One then obtains the accelerations $a_{wv,Head}$ for the head from the translational movements in the three spatial directions, $a_{wv,Rot}$ for the head from the rotational movements about the spatial directions, and $a_{wv,S}$ for the seat from the translational movement, the latter possibly also as a reference for plausibility checking.
- This is followed by the calculation S6 of the input-specific RMS values, weighted in a manner dependent on magnitude, to form an overall value $a_{wv,overall}$ of the acceleration.
- The overall value $a_{wv,overall}$ of the acceleration is subsequently made available, for example (i) for a classification of the overall value into a category of a comfort scale, in particular with stages of not comfortable (0) to comfortable (6), (ii) for control of a vehicle control system 20, as illustrated for example in conjunction with FIGS. 1 and 2, and/or (iii) for the planning, development and production of vehicle components.
- In an interposed and possibly optional step S5, reference values for movements may be made available and/or determined and jointly or alternatively taken into consideration as so-called c and d values. This may serve for example for checking the plausibility of the movement of an occupant 1'. The c value is in this case a predetermined threshold value for the assessment of the vehicle movement from the acceleration value $a_{wv,S}$, for example by measurement and evaluation in the region of a vehicle seat 60.
- An undershooting or overshooting of the threshold value c by a measure for the vehicle movement defines, in step S5, which upper limit d1, d3 or d2, d4 is selected as a maximum value or capping limit for the consideration of accelerations $a_{wv,Head}$ for the head from the translational movements in the three spatial directions and $a_{wv,Rot}$ for the head from the rotational movements about the spatial directions in the calculation of the overall acceleration $a_{wv,overall}$.
- If, for example, the specified threshold value c is thus overshot by the determined overall acceleration $a_{wv,S}$ of the vehicle seat 60, that is to say the vehicle moves with relatively great intensity, the value d1 is used as a threshold value or upper limit for the overall acceleration $a_{wv,Head}$ determined at the head of the occupant. In the subsequent calculations, $a_{wv,S}$ and $a_{wv,Head}$ are used as calculated, the latter specifically on the basis of the c value up to the selected maximum value d1.
- The value d1 thus functions as a form of capping limit or saturation value, and values for the acceleration $a_{wv,Head}$ are taken into consideration only up to this maximum limit d1.
- A corresponding description applies for the situation if the c value is undershot. In this case, the value d2 is taken into consideration as a maximum value for the acceleration $a_{wv,Head}$. An analogous description applies for the rotational movement, the overall acceleration $a_{wv,Rot}$ determined in that case from rotational components relating to the head, and maximum values d3, defined for this, for an overshooting of the c value or d4 for an undershooting of the c value.

The method according to embodiments of the invention have, individually or in combination, the following advantages in relation to the conventional approach, in particular in relation to the approach according to the ISO-2631 standard:

- Additional measurement points, in particular at the head 3 of an occupant 1' for the purposes of detecting head movements, can be taken into consideration, for example also further measurement points on the chest and thighs or other regions 2 on the body 1 of the occupant 1'.
- Biometric measurement values or variables can be incorporated, for example height, weight, age, gender and the like.
- A comfort scale with exactly defined range boundaries can be provided, wherein the intervals or range boundaries in particular do not overlap but adjoin one another. A six-stage scale is conceivable.
- A weighting of the individual movements, rotations and/or vibrations or of the RMS values in accordance with input value or input channel may be performed, which is dependent on the magnitude or intensity of the movement and of the respective RMS value.
- In addition or alternatively, the present invention also relates to the use of mathematical methods and/or models for calculating (i) the limits, limit values or threshold values, which are also referred to as a, c and d values, and the selection of the weighting factors, the selection of the d values as maximum values or capping limits in the consideration of acceleration values to form the overall acceleration, or themselves serving as maximum values or capping limits, (ii) the weighting factors or k values themselves, and/or (iii) the range boundaries of the comfort scale, which are also referred to as b values.

Such mathematical methods may for example be the k-means method or other clustering methods, for example for determining or calculating the a, b, c and d values and the use of optimization methods, for example trial and error methods and/or brute force methods, for example for determining the k values. It is however possible for all methods to be used individually or in a selected combination for determining respective parameters a, b, c, d and k in embodiments of the present invention.

Alternatively or in addition, the values may be determined empirically or partially empirically.

A further embodiment takes into consideration the use of substitute models by regression, machine learning methods, neural networks and the like. On the basis of the defined inputs or input values (determined from the movements) and the outputs or output values (comfort value), artificial systems can be generated. These may also be trained from a model such as that proposed here. An advantage here is that the substitute models are often faster-acting.

As has already been indicated above, an additional or alternative further aspect of the present invention can be seen in a consideration of personal and/or biometric data for calculating the comfort value.

This may be performed in particular under the influence of the weighting factors or k values.

For this purpose, use may be made inter alia of biometric data—such as height, age, weight, gender etc.

These may be compiled and/or determined inter alia by way of sensors in seats 60, cameras or other sensor units 10 and/or through an incorporation of digital personal profiles, for example by way of a smartphone and/or from social networks.

The data for creating the model may be obtained by way of field tests and studies in a real vehicle and/or driving simulator.

Empirical tests and/or mathematical approaches may also be used for the corresponding calculation of the a, k and b values.

The approach according to embodiments of the invention has inter alia the following advantages:

It results in greater objectification of the assessment of driving comfort, and this can be a basis for measures for improving the comfort.

Furthermore, greater accuracy is obtained with the enhanced model in relation to the ISO-2631 standard, in particular in conjunction with the calculation of upper and lower limits.

Further measurement points are conceivable as relevant measurement points in the case of autonomous driving, in particular in the region 2 of the head 3 of an occupant 1'.

There is the possibility of a clear definition of boundaries of the ranges of a comfort scale, and this further increases the degree of possible objectification.

Increased flexibility of the approach according to embodiments of the invention and of the underlying model is also possible, in particular through value-dependent and/or magnitude-dependent weighting in the determination of an overall acceleration.

Calculation of the required a, b and/or k values by mathematical methods further increases the degree of possible objectification, specifically in turn in relation to the ISO-2631 standard, in which exclusively previously specified values are used as weighting factors.

The incorporation of individual personal data further increases the reliability and the flexibility of the method according to embodiments of the invention.

Furthermore, in the case of automation, the required processing time is considerably shorter than in the case of a conventional method with live evaluation and consideration.

LIST OF REFERENCE DESIGNATIONS

1 Body
1' Occupant
2 Region of the body
3 Head
4 Viewing direction
10 Sensor, sensor unit
20 Vehicle control system
21 Actuator
50 Control unit
51 Control and/or detection line
52 Control and/or detection line
60 Seat
70 Console, dashboard
80 Steering wheel
100 Vehicle, motor vehicle
x Spatial direction, translation direction rotational axis
y Spatial direction, translation direction rotational axis
z Spatial direction, translation direction rotational axis

What is claimed is:

1. An operational assistance method for a vehicle, the method comprising:
    measuring, by a sensor, movements of a region of a body of a vehicle occupant, wherein the movements comprise at least one of a translational movement or a rotational movement of the region of the body of the vehicle occupant,
    providing sensor values representative of the movements, wherein the sensor values comprise acceleration values of the region of the body of the vehicle occupant, and the acceleration values are determined from the movements,
    weighting the sensor values with respect to one another,
    combining the weighted sensor values to form an overall acceleration value, and
    providing the overall acceleration value,
    wherein a weighting factor for a respective sensor value of the sensor values as a degree of a weighting of the respective sensor value in the overall acceleration value is dependent on a magnitude of the respective sensor value.

2. The method according to claim 1, wherein the vehicle is a motor vehicle.

3. The method according to claim 1, wherein, in a manner dependent on the magnitude of the respective sensor value, the weighting factor for the respective sensor value is selected from a set of a plurality of weighting factors based on a single-stage or a multi-stage comparison of the magnitude of the respective sensor value with one or more limit values.

4. The method according to claim 3, wherein the weighting factor is selected based on a single-stage or a multi-stage comparison of the magnitude of the respective sensor value with one or more limit values.

5. The method according to claim 1, wherein the sensor values are determined as RMS values.

6. The method according to claim 5, wherein the sensor values are determined with bandpass filtering.

7. The method according to claim 5, wherein the sensor values are determined separately for each spatial degree of freedom.

8. The method according to claim 1, wherein the sensor values for translational and for rotational degrees of freedom are in each case separately combined with one another in each case as an RMS value.

9. The method according to claim 1, wherein at least one of a head, one or more limbs, a chest, or thighs of an occupant is the region of the body.

10. The method according to claim 1, wherein:
the overall acceleration value is assigned a comfort value from a comfort scale with a plurality of disjoint intervals of acceleration values with interval limits, and
the interval limits are determined by way of a clustering method and by way of a K-means method.

11. The method according to claim 10, wherein the comfort scale is discrete.

12. The method according to claim 1, wherein at least one of:
limit values for a single-stage or a multi-stage comparison for at least one of determination or selection of weighting factors are determined by way of a clustering method, or
the weighting factors are determined by way of at least one of an optimization method, a brute force method, or a trial and error method.

13. The method according to claim 12, wherein the clustering method is a K-means method.

14. The method according to claim 1, wherein at least one of the overall acceleration value, a comfort value, or a signal derived from the at least one of the overall acceleration value or the comfort value, at least one of:
is supplied to a vehicle control system, or
is used for at least one of determining a chassis model or in a production method.

15. The method according to claim 14, wherein at least one of the overall acceleration value, the comfort value, or the signal derived from the at least one of the acceleration value or the comfort value is supplied to an actuator of the vehicle for operational control of the vehicle.

16. The method according to claim 15, wherein at least one of the overall acceleration value, the comfort value, or the signal derived from the at least one of the overall acceleration value or the comfort value is supplied to the actuator of the vehicle for damping control of the vehicle.

17. A control unit for a vehicle, wherein the control unit is configured to at least one of initiate, trigger, execute, or control in open or closed-loop fashion the method according to claim 1.

18. A vehicle comprising the control unit according to claim 17.

* * * * *